US00PP18763P2

(12) United States Plant Patent
Hanson et al.

(10) Patent No.: US PP18,763 P2
(45) Date of Patent: Apr. 29, 2008

(54) ***HELIOPSIS* PLANT NAMED 'TUSCAN SUN'**

(50) Latin Name: *Heliopsis helianthoides*
Varietal Denomination: Tuscan Sun

(76) Inventors: Brent Hanson, 502 N. Stevens St., Rhinelander, WI (US) 54501; David Charles Zlesak, 1500 Fairmount Ave., St. Paul, MN (US) 55105

( * ) Notice: Subject to any disclaimer, the term of this patent is extended or adjusted under 35 U.S.C. 154(b) by 24 days.

(21) Appl. No.: 11/493,056

(22) Filed: Jul. 25, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Louanne Krawczewicz Myers

(57) ABSTRACT

A new cultivar of *Heliopsis helianthoides* 'Tuscan Sun' characterized by its compact plant habit, sturdy stems, green leaves and stems, and golden-yellow ray flowers. In combination these traits set 'Tuscan Sun' apart from all other existing varieties of *Heliopsis* known to the inventors.

3 Drawing Sheets

Genus: *Heliopsis.*
Species: *helianthoides.*
Denomination: 'Tuscan Sun'.

BACKGROUND OF THE INVENTION

The present invention relates to a new and distinct cultivar of Ox Eye Sunflower, a herbaceous perennial that is grown for use as an ornamental landscape and container plant. The new invention is known botanically as *Heliopsis helianthoides* and will be referred to hereinafter by the cultivar name 'Tuscan Sun'. *Heliopsis* is in the family Asteraceae under which the commonly referred to "flower" is actually the inflorescence, and made up of smaller ray florets and disc florets. The ray florets are what look like "petals". For ease of clarification the common term "flower" is used herein to describe the inflorescence.

'Tuscan Sun' is a chance seedling that was discovered by the inventors in 1997 amongst many open-pollinated seedlings of *Heliopsis helianthoides* (unpatented) in a cultivated garden in Rhinelander, Wis. Adjacent to the cultivated garden was a planting of stock plants of *Heliopsis helianthoides* 'Loraine Sunshine' (U.S. Plant Pat. No. 10,690). The inventors consider that there is a high probability that 'Loraine Sunshine' is a parent of 'Tuscan Sun'. 'Tuscan Sun' differs from 'Loraine Sunshine' in that it has solid green leaves and a very compact habit.

The combined characteristics of 'Tuscan Sun' are: compact plant habit, sturdy stems, green leaves and stems, and golden-yellow ray flowers. These characteristics make this new cultivar unique and unlike any other known cultivars of *Heliopsis helianthoides* known to the inventors. Although there are cultivars that exist with variation in plant height, plant form, inflorescence, leaf and stem color, and ray floret number, no cultivars known to the inventors have as compact of a plant habit as 'Tuscan Sun'.

The first asexual reproduction of 'Tuscan Sun' was carried out by the inventors in 1999 in Rhinelander, Wis. The method used for asexual propagation was vegetative cuttings. Since that time the inventors have determined that distinguishing characteristics of 'Tuscan Sun' are stable and are reproduced true to type in successive generations of asexual reproduction.

SUMMARY OF THE INVENTION

The following traits have been repeatedly observed and represent the distinguishing characteristics of the new *Heliopsis* cultivar. These traits in combination distinguish 'Tuscan Sun' from all other existing varieties of *Heliopsis* known to the inventors. 'Tuscan Sun' has not been tested under all possible conditions and phenotypic differences may be observed with variations in environmental, climatic, and cultural conditions, however, without any variance in genotype.

1. *Heliopsis* 'Tuscan Sun' is an herbaceous perennial.
2. *Heliopsis* 'Tuscan Sun' exhibits a compact upright habit.
3. *Heliopsis* 'Tuscan Sun' exhibits large daisy-like inflorescence.
4. *Heliopsis* 'Tuscan Sun' inflorescenses are bright golden-yellow in color.
5. *Heliopsis* 'Tuscan Sun' is long blooming from early summer to early fall.
6. *Heliopsis* 'Tuscan Sun' has medium-green foliage and stems.
7. *Heliopsis* 'Tuscan Sun' stems are sturdy and wind tolerant.
8. *Heliopsis* 'Tuscan Sun' is up to 0.6 m in height and width.
9. *Helioposis* 'Tuscan Sun' is reproduced asexually.
10. *Heliopsis* 'Tuscan Sun' is hardy to USDA Zone 3–8.

BRIEF DESCRIPTION OF THE DRAWINGS

The accompanying drawings illustrate the overall appearance of the new *Heliopsis* plant 'Tuscan Sun' showing the colors as true as it is reasonably possible to obtain in colored reproductions of this type. Colors in the drawings may differ from the color values cited in the detailed botanical description, which accurately describes the actual colors of the new variety 'Tuscan Sun'. The drawings were made of plants that were grown in an outdoor trial bed in St. Paul, Minn. The plants were three years old grown from rooted stem cuttings.

The drawing labeled as FIG. 1 shows the plant habit when primary and secondary flower heads have some individual disk florets at anthesis.

Figure 1:
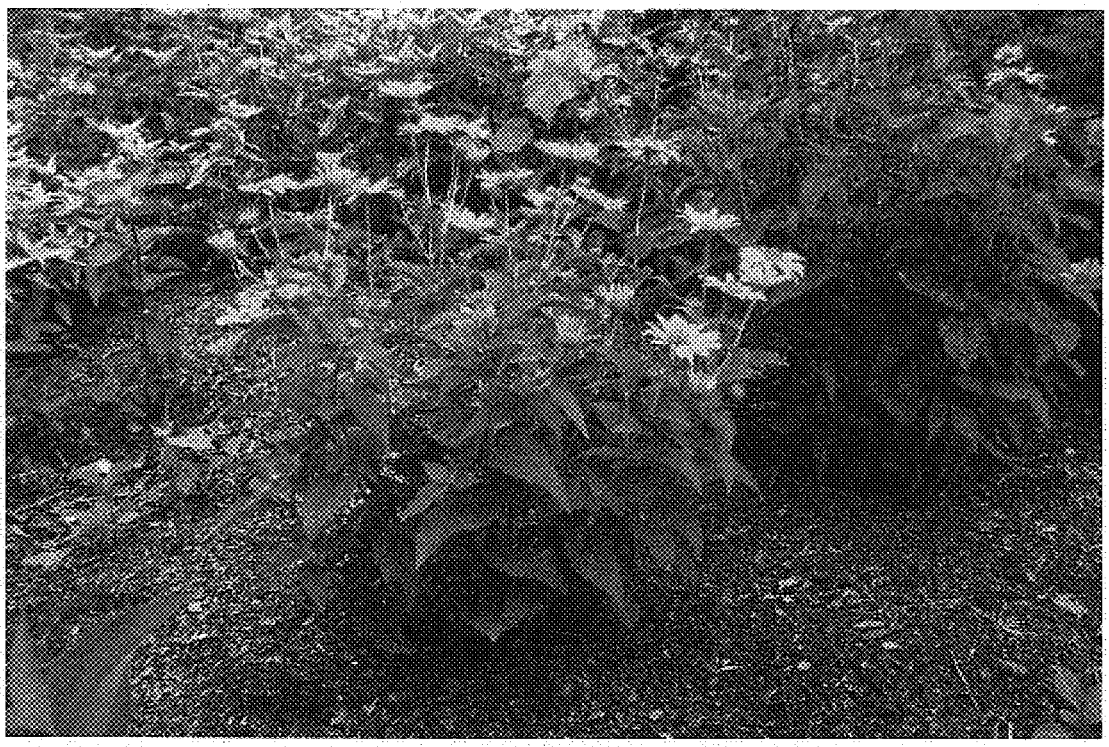
Figure 2:
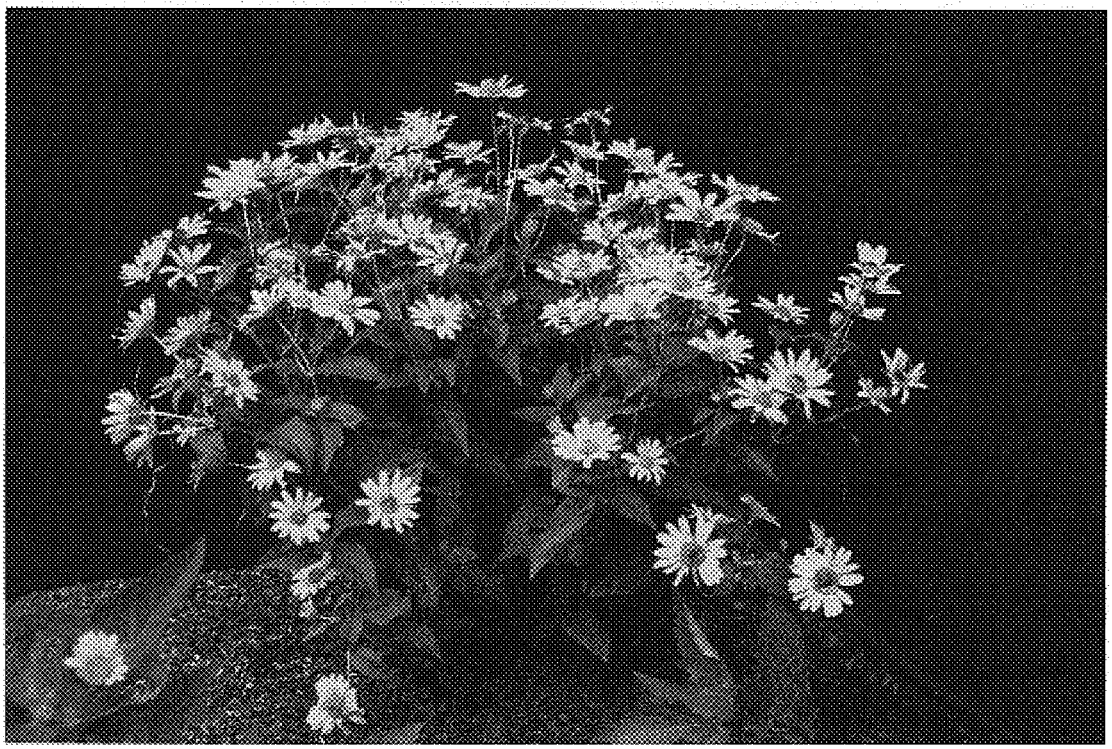

The drawing labeled as FIG. 2 shows the plant habit of 'Tuscan Sun' when in peak bloom.

Figure 3:
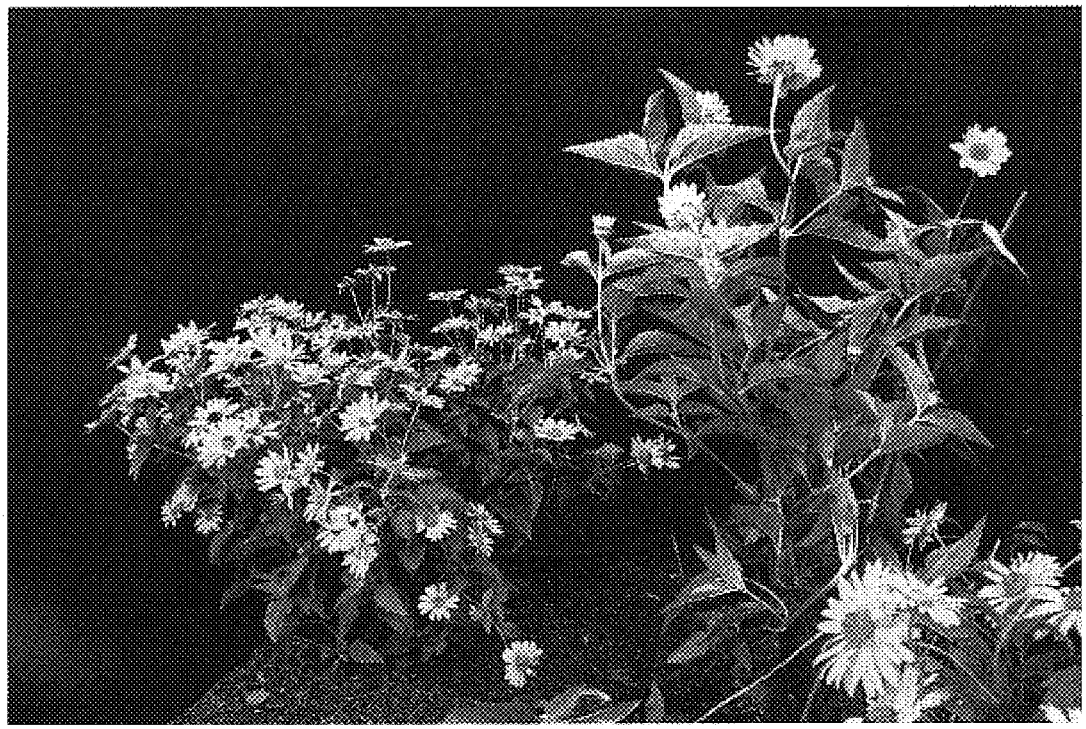

The drawing labeled as FIG. 3 shows the plant habit of 'Tuscan Sun' (depicted on the left) when in peak bloom with a *Heliopsis helianthoides* seedling that has a typical height of approximately 90 cm growing adjacent to 'Tuscan Sun' for comparison.

Figure 4:
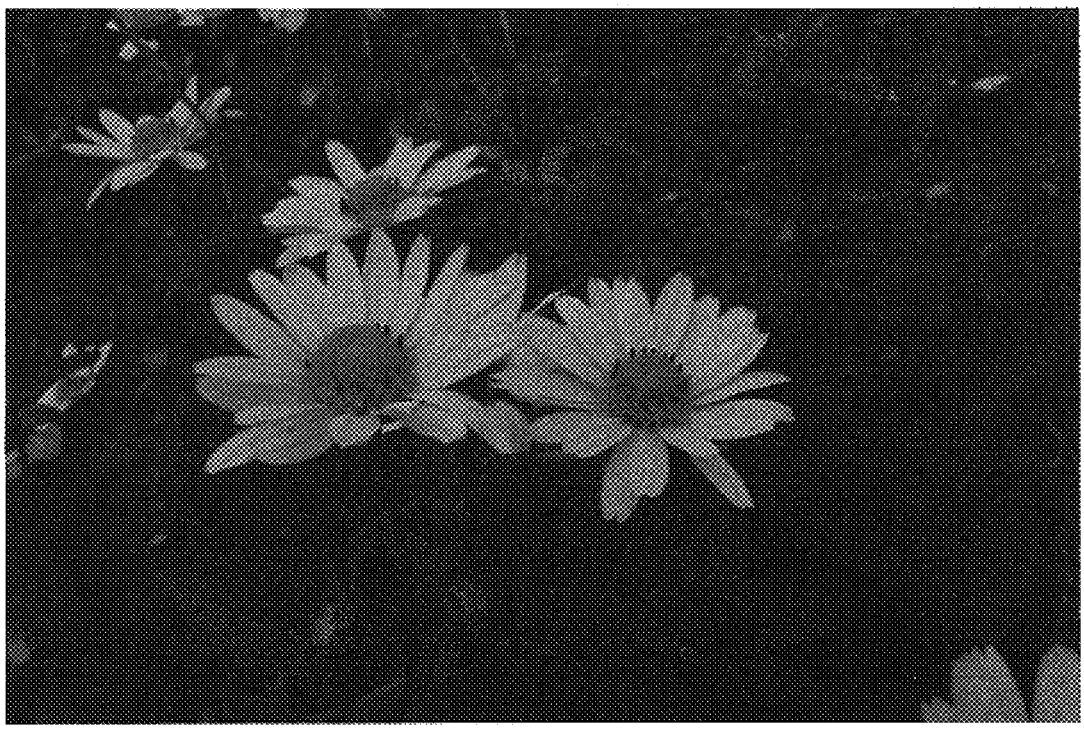

The drawing labeled as FIG. 4 shows a close-up of flower heads of 'Tuscan Sun' with disk florets shedding pollen.

Figure 5:
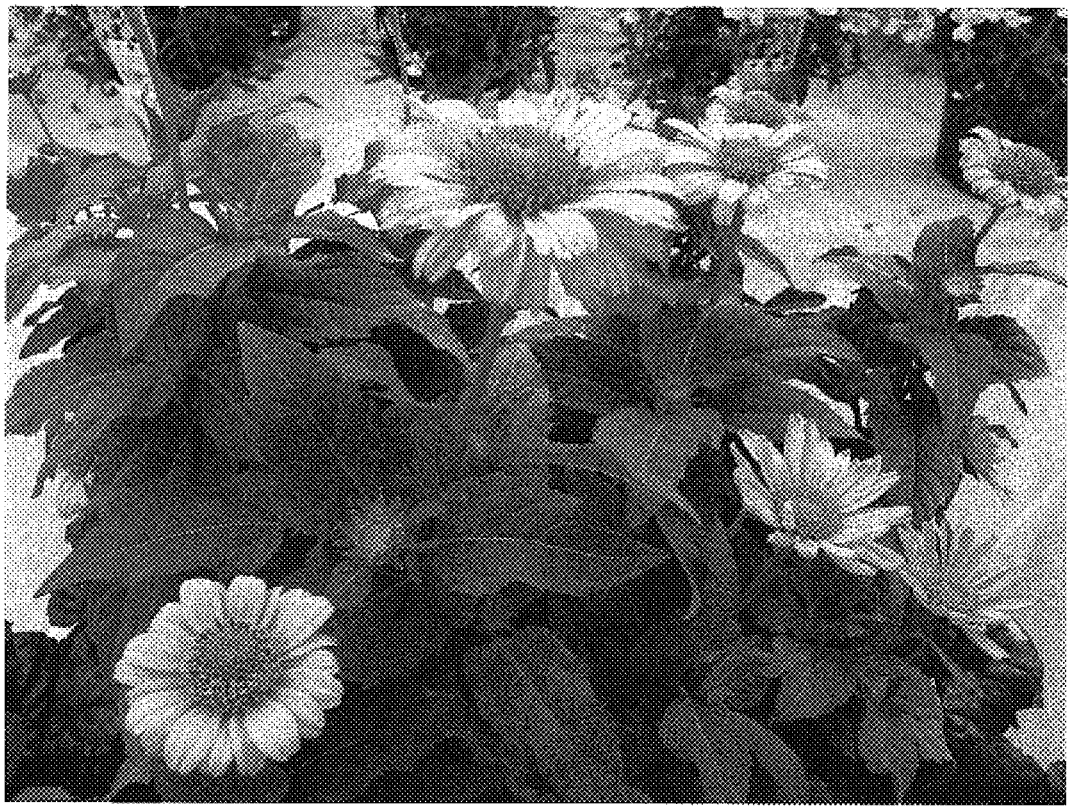

The drawing labeled as FIG. 5 shows flower heads of 'Tuscan Sun' with disk florets shedding pollen, foliage, and unopened secondary flower heads.

Drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new *Heliopsis* cultivar 'Tuscan Sun'. Observations, measurements, values and comparisons were compiled in St. Paul, Minn., from a two year old plant grown in a trial bed. Color determinations are made in accordance with The 1995 Royal Horticultural Society Colour Chart from London, England, except where general color terms of ordinary dictionary significance are used. In the Asteraceae family, under which *Heliopsis* is classified, the commonly referred to "flower" is actually the inflorescence, and made up of smaller ray florets and disc florets. For ease of clarification the common term "flower" is used here to designate a category of description. Under this category is the detailed botanical description of the parts of the inflorescence, which is commonly referred to as the "flower" of this plant.

Botanical classification:
- *Genus.*—*Heliopsis.*
- *Species.*—*Helianthoides.*
- *Cultivar.*—'Tuscan Sun'.
- *Common name.*—Ox Eye Sunflower.

Parentage: *Heliopsis* 'Tuscan Sun' is a chance seedling that resulted from the open pollination of *Heliopsis helianthoides.*

Propagation method: Division, vegetative terminal and internode stem cuttings, and tissue culture.

Root description: Fibrous, fine and well-branched.

Vigor: Vigorous.

Root initiation: 10 days to 2 weeks at 70 degree F. air temp in summer.

Time required for root development: 8 weeks to fully develop in a 50 cell in soil-less media when grown at 70–80 degree F. in a greenhouse without supplemental lighting in summer.

Crop time: 3–4 weeks are needed to produce a finished 4-inch container and approximately 8 weeks are needed to produce a finished 2-litre container from a rooted cutting.

Growth habit: Upright and compact habit.

Use: Ornamental landscape plant or container plant.

Type: Herbaceous perennial.

Dimensions: Up to 0.6 m in height and 0.6 m in width.

Cultural requirements: Tolerant of a wide range of growing conditions, grows well in full sun to light shade, in dry to moist soils.

Hardiness: USDA Zone 3–8.

Pest and disease susceptibility: Relatively disease free. No susceptibility or resistance to diseases or pests have been observed for 'Tuscan Sun'.

Stem:
- *Branching habit.*—Loosely branched.
- *Stem color (primary and lateral).*—New growth, 144B; mature growth, 144B.
- *Stem dimensions.*—Approximately 50 cm in length and 5 mm in diameter with lateral branches approximately 25 cm in length and 2 mm to 3 mm in diameter.
- *Stem shape.*—Round.
- *Stem strength.*—Firm, stiff.
- *Stem surface.*—Mature stems are glabrous; stems of new growth have fine white hairs.
- *Internode length.*—5.0 cm to 9.0 cm in length.

Foliage:
- *Type.*—Evergreen.
- *Leaf arrangement.*—Opposite.
- *Single or compound.*—Single.
- *Leaf division.*—Simple.
- *Leaf.*—Margin: Serrate. Shape: Ovate. Dimensions: 6 cm to 10 cm in length, 3 cm to 4 cm in width. Base: Variable ranging from primarily cordate for leaves attached to the primary stem to cuneate for leaves attached to secondary and tertiary stems. Apex: Acute. Venation pattern: Tri-nerved. Vein color (both surfaces, immature and mature): 138C. Color (abaxial surface): Immature: between 138A and 138B; Mature: 138B. Color (adaxial surface): Immature: between 139A and 139B; Mature: between 137A and 137B. Surface (abaxial surface): Very fine, short hairs. Surface (adaxial surface): Scabrous.
- *Leaf attachment.*—Petiole.
- *Petiole dimensions.*—3 mm to 20 mm in length, 2 mm to 3 mm in width.
- *Petiole shape.*—Rounded on lower surface and flat on upper surface.
- *Petiole color.*—Intermediate between 138C and 139D in color.
- *Fragrance.*—None.

Flower:
- *Inflorescence.*—Capitulum: heterogamous with ray florets around the head margin and disk florets in the center, forming a radiant head. Single capitulum per terminal arising from leaf axils.
- *Aspect.*—Facing upward.
- *Dimensions of inflorescence.*—1 cm in depth and 5.5 cm to 6.5 cm in diameter from the apex of one ray floret to the apex of the opposite ray floret.
- *Diameter of disc.*—Ranges from 1.6 cm to 2.0 cm.
- *Quantity of inflorescences per terminal.*—One.
- *Flower shape.*—Saucer-shaped.
- *Quantity of flowers and buds per plant.*—Numerous, in excess of 100.
- *Natural flowering season.*—Early summer to early fall (June through September).
- *Lastingness of boom on plant.*—About 30 days until senescence of ray florets; disk florets are persistent.
- *Fragrance.*—None.
- *Peduncle.*—Dimensions: 5 cm to 9 cm in length, approximately 2 mm in diameter. Surface: Pubescent with very fine hairs. Color: 139C. Strength: Flexible.
- *Bud.*—Shape: Cup shaped. Dimensions: Up to 8 mm in diameter. Phyllary color: Between 144A and 145A.

*Self-cleaning or persistent.*—Ray florets are self-cleaning; disk florets are persistent.

*Involucral bracts or phyllary* (*calyx*).—Number: 18 to 24 per inflorescence. Dimensions: 9 mm to 12 mm in length; 3 mm to 5 mm in width. Fused or unfused: Fused. Margin: Entire. Color (both surfaces): Between 144A and 145A. Apex: Acute. Shape: Ovate. Texture: Pubescent.

*Ray floret.*—Number: 13 to 22 per inflorescence. Shape: Oblong with 2 recessed ribs running vertically. Dimensions: 2 cm to 3 cm in length and 0.8 cm to 1 cm in width. Apex: Retuse. Base: Attenuate. Margins: Entire. Aspect: Flat. Texture: Glabrous. Fused or unfused: Fused. Color (abaxial): Opens between 15B and 17C, matures to 7B. Color (adaxial): Opens 17B, matures to 13B. Sex: Gynoecium only.

*Disc florets.*—Number: Many, in excess of 100. Dimensions: 7 mm to 10 mm in length, 1 mm in width. Shape: Tubular. Apex: Retuse. Base: Tubular base which connects directly to ovary. Margin: Same as apex. Texture: Glabrous. Color (both inner and outer surfaces): 144B towards the base and 163A towards the apex. Sex: Gynoecium and androecium both present.

Reproductive organs:

*Stamens.*—5 fused.

*Stamen dimensions.*—2 mm in length, and 0.25 mm in width.

*Anther shape.*—Linear.

*Anther dimensions.*—2 mm in length.

*Anther color.*—Between 166A and 200C.

*Quantity of pollen.*—Moderately abundant.

*Pollen color.*—14A.

*Pistil dimensions.*—4 mm in length, and 0.3 mm in width.

*Stigma shape.*—Bifid.

*Stigma color.*—15B.

*Style color.*—15B.

*Style dimensions.*—5 mm. in length and 0.50 mm in width.

*Style shape.*—Filament.

*Ovary.*—Inferior.

*Ovary dimensions.*—4 mm in length, 2 mm in width.

*Ovary shape.*—Triangular.

*Ovary color.*–145A with the top 200D.

Fruit:

*Type.*—Achene.

*Dimensions.*—4 mm in length, 1 mm in width.

*Color.*—Variable; ranges between 200A to 200D.

Seed: 'Tuscan Sun' is self-incompatible. In the absence of other *heliopsis*, no viable seeds have been observed.

It is claimed:

1. A new and distinct cultivar of *Heliopsis* plant named 'Tuscan Sun' as described and illustrated.

* * * * *